United States Patent [19]

Stundel et al.

[11] Patent Number: 4,996,989
[45] Date of Patent: Mar. 5, 1991

[54] ELECTRODE

[75] Inventors: Avram Stundel, Brooklyn, N.Y.; Frank Avellanet, Westport, Conn.

[73] Assignee: Bodylog, Inc., Mt. Kisco, N.Y.

[21] Appl. No.: 556,861

[22] Filed: Jul. 19, 1990

Related U.S. Application Data

[63] Continuation of Ser. No. 368,160, Jun. 15, 1989, abandoned, which is a continuation of Ser. No. 936,639, Apr. 13, 1987, abandoned.

[51] Int. Cl.$^5$ .......................................... A61B 5/0402
[52] U.S. Cl. ..................................... 128/639; 128/644
[58] Field of Search ................................ 128/639–641, 128/644, 758, 802, 803

[56] References Cited

U.S. PATENT DOCUMENTS

| | | | |
|---|---|---|---|
| 2,318,207 | 5/1943 | Ellis | 128/644 |
| 2,555,037 | 5/1951 | Jensen | 128/639 |
| 3,085,577 | 4/1963 | Berman et al. | 128/641 |
| 3,542,010 | 11/1970 | Love | 128/644 |
| 3,976,055 | 8/1976 | Monter et al. | 128/644 X |
| 4,350,165 | 9/1982 | Striese | 128/640 |
| 4,441,501 | 4/1984 | Parent | 128/641 |

Primary Examiner—Lee S. Cohen
Attorney, Agent, or Firm—Stephen E. Feldman

[57] ABSTRACT

An electrode in the form of a conductive balloon is mounted in a head or other body part band. An open face flange with teeth accurately spaced about the flange is secured to the headband. The teeth extend through the head band from one side and fit into spaced slots or holes in a back plate located on the other side of the headband. A portion of the headband is captured by the teeth between the flange and the back plate. A conductive fabric is held between the open face flange and the headband and covers the opening in the flange. When the flange and back plate are drawn or pressed together and held by the teeth secured in the openings in the back plate part of the captured part of the headband is forced out of the opening in the flange. Since the conductive fabric covers the opening in the flange the conductive fabric is pushed upwards by the headband material forced out of the flange opening forming a conductive balloon electrode.

29 Claims, 2 Drawing Sheets

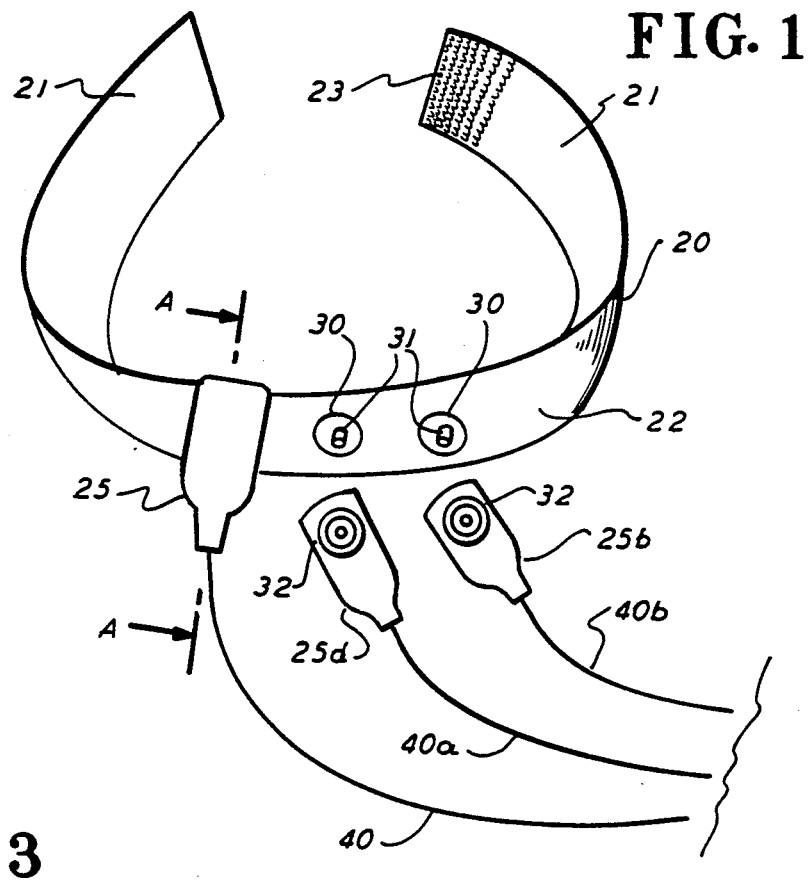
FIG. 1
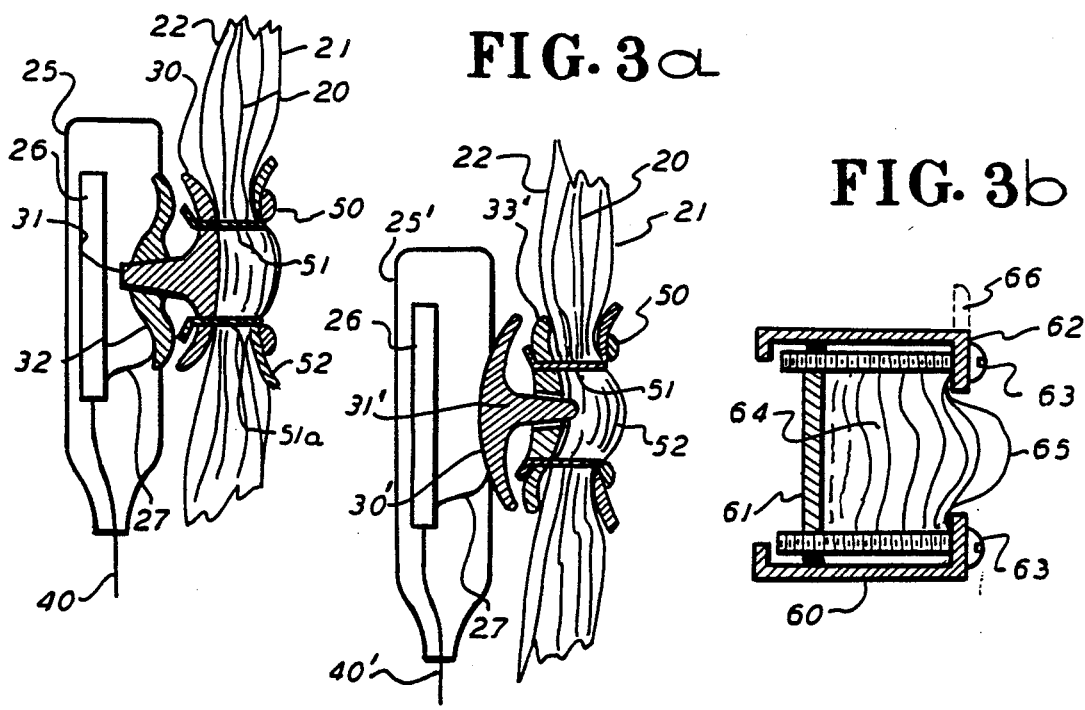
FIG. 3
FIG. 3a
FIG. 3b

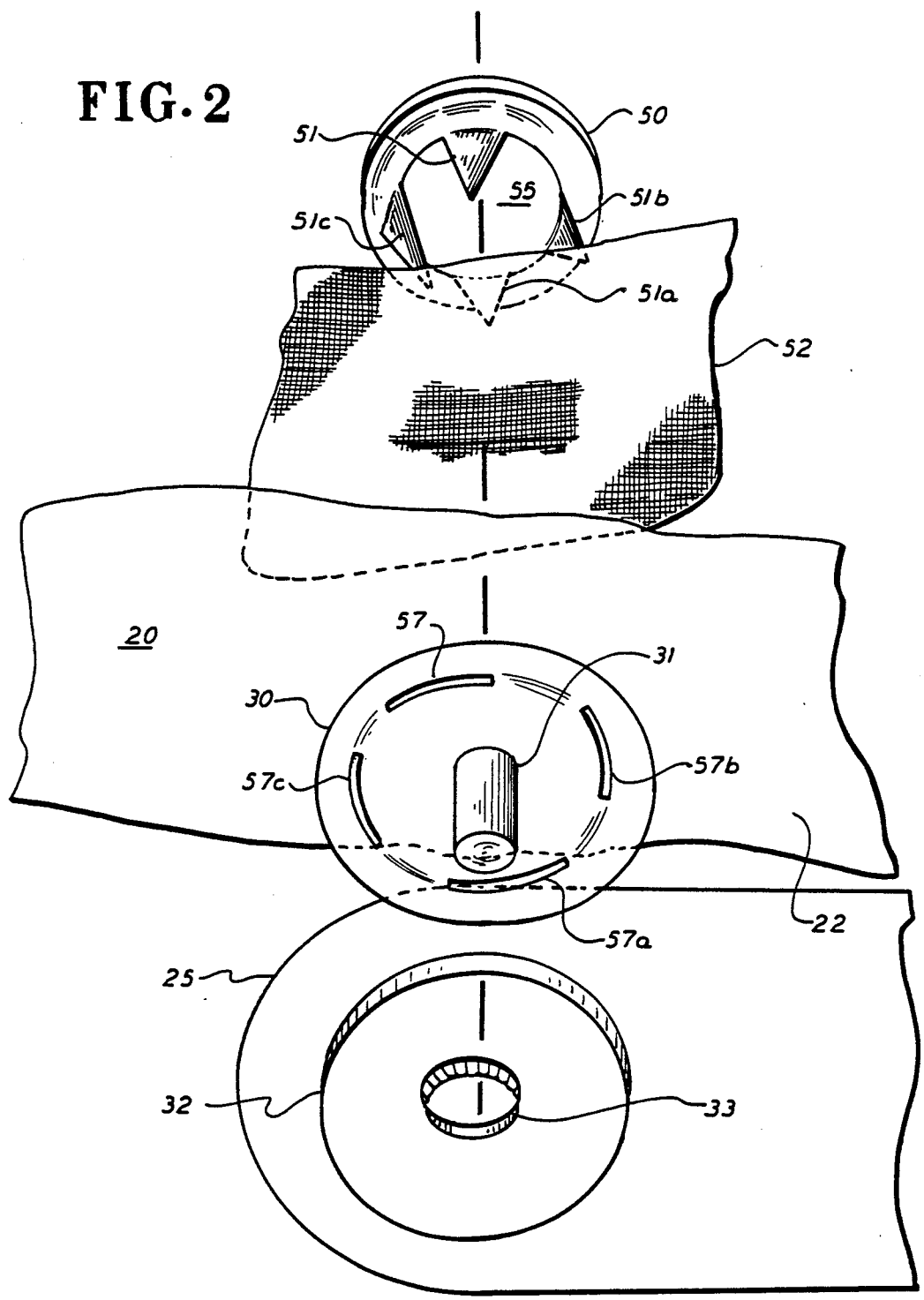

ELECTRODE

This application is a continuation, of application Ser. No. 07/368,160 filed June 15, 1989, now abandoned, which is a continuation of application Ser. No. 06/936,639, filed Apr. 13, 1987, now abandoned.

BACKGROUND OF THE INVENTION

1. Field of the Invention

This invention relates to electrodes used for making contact with the surface or skin of the body, for monitoring and/or picking up electric impulses generated by the various parts of the body.

The class of electrodes to which the present invention is related finds great utility in medicine, for example, for diagnostic purposes such as for monitoring and/or picking up electric impulses generated by brain activity, i.e. brain waves for the electroencephalogram (E.E.G.) or for picking up electric impulses generated by heart activity for the electrocardiogram (E.K.G.). More recently electrodes have been used to pick up electric impulses generated by body parts for monitoring a patient in intensive care hospital units. A more recent use of electrodes is for the purpose of picking up electric impulse generated by muscular activity during exercise and/or skill enhancement activities for monitoring muscular activity, one purpose being for tuning coordination of interacting muscular activity, for example.

2. Prior Art

The class of electrodes to which the present invention is related is normally used to pick up electric information, such as electric impulses generated by the body, which directly relate to some body activity. This information need be accurate as possible, especially when the information is used for medical diagnostic purposes. The electric impulses generated by the body are very small and the body itself is a poor conductor. In order to accurately detect the body electric impulses good electrical conductivity between the electrode and the skin is most desirable. In order to achieve good electrical conductivity between the skin of a person on whom the electrode is used and the electrode element, many electrodes use suction cups to draw the skin into tight, intimate contact with the electrode. This suction on the skin is uncomfortable, especially if the electrode/suction cup combination is used over an extended period of time. Another technique used to achieve better electric contact is the use of conductive fluids and/or ointments in conjunction with the electrode. This is messy and often not practical.

U.S. Pat. No. 4,391,279 to Stein is an example of the prior art which discloses an electrode made in suction cup form. Stein's structure calls for the use of a conductive silicone rubber for the suction cup. A metal electrode in rivet configuration passes through the center of the suction cup and terminates in the form of a stud of a snap on fastener. Stein also suggests that the skin of the patient on whom his electrode is used, be coated with conductive gel or water to enhance conductivity. An earlier prior art U.S. Pat. No. 2,895,479 issued to Lloyd discloses an electrode which uses a sintered or porous metal disc over which a reservoir for a fluid is positioned. The reservoir is filled with water soluble electrolytes to overcome resistance of the skin and improve contact between the skin and the electrode. The electrode disclosed by Corbett in U.S. Pat. No. 4,537,198 provides for a sponge element to be attached to the electrode and saturation of the sponge by use of a conductive fluid is called for to enhance conductivity.

GENERAL DESCRIPTION OF THE PRESENT INVENTION

The present invention is a novel structured electrode, the preferred embodiment of which is used with a band, such as a headband, arm band, wrist, leg or chest band or other, for example, hereinafter referred to as headband, in which the electrode element comprises an open face flange with teeth or prongs located peripherally around the flange for inserting into the headband. Preferably the headband is of a resilient material. A conductive material, such as a metal impregnated fabric, for example, is located between the under surface of the open face flange and the material of the headband and is secured in place by the teeth penetrating the conductive material. Penetration of the conductive material by the teeth of the flange serves as an electric connection between the flange/teeth and the conductive material and holds the conductive material in place. The teeth of the open face flange extend through the conductive material, material of the headband and into receiving ports or openings of a back plate which may be in the form of a socket plate or stud plate of a snap fastener. The teeth or prongs are inserted into the receiving ports which are spaced around the backplate and, when bent over the exposed surface of the plate, secure the plate to the other side of the headband and provide an electric connection between the back plate and to the open face flange. In securing the open face flange, on one side of the headband, to the back plate, on the other side of the headband by the peripherally located prongs or teeth extending from the flange, the headband is compressed between the open face flange on one side of the headband and the back plate on the other side of the headband, effectively squeezing that portion of the headband between these two elements up and out of the open area of the face of the flange. With the conductive material exposed in the open face of the flange, the conductive material is pushed in balloon-like fashion or pushed to balloon out of the opening in the open face flange and forms a conductive balloon raising above the exposed surface of the open face flange.

When the conductive material is a silver or silver chloride impregnated fabric, good conductivity between the skin and the electrode is achieved. Other metal impregnated fabrics such as carbon or stainless steel impregnated fabric, for example, may be used and achieve good conductivity; however, silver or silver chloride impregnated fabrics are preferred since these metals provide good electrical contact with the skin. Preferably the headband is a pliable material with resiliency so that the material, when compressed between the open face flange and the back plate will tend to expand to its normal state through the open face of the flange thus ballooning beyond the upper surface of the flange forming a conductive balloon.

This high crown, convex contour of this novel structured electrode overcomes the discomfort caused by the suction cup structure electrode and provides good conductive contact with the skin. The conductive crown or conductive balloon has a surface of highly conductive fabric which may be firmly pressed against the skin without discomfort to the patient. Good conductive contact is achieved without the need of conductive fluids or ointments and avoids the mess and clean up required when conductive fluids are used. It will also be appreciated that when the conductive balloon makes connection with the skin the balloon may mushroom somewhat providing more surface contact with the skin.

OBJECTS OF THE INVENTION

It is an object of the invention to provide an electrode which makes good conductive contact with the skin while avoiding the use of suction cups and conductive fluids.

Another object is to provide a conductive balloon electrode which reaches toward the patient from the band and achieves comfortable contact.

Another object is to provide an open faced electrode with a conductive balloon extending out of the face of the electrode.

A further object is to provide a high, conductive crown electrode which is secured to a headband by a plurality of connectors which are secured or attached to one member of a two-part snap fastener.

Additional objects and advantages of the invention will become apparent as the following detailed description of the invention is read in conjunction with the accompanying drawing which illustrate a preferred embodiment and alternate embodiments of the invention.

BRIEF DESCRIPTION OF THE DRAWINGS

FIG. 1 is a pictorial representation of three headband mounted electrodes of the present invention with snap on printed circuit connectors.

FIG. 2 is an exploded view of the preferred embodiment of the electrode of the present invention.

FIG. 3 is a sectional view of the electrode along line A—A of FIG. 1.

FIG. 3a is a sectional view of an alternate structure of the electrode along line A—A of FIG. 1.

FIG. 3b is a sectional view of another form of the invention, without the band.

DETAILED DESCRIPTION OF THE PREFERRED EMBODIMENT OF THE INVENTION

Referring to FIG. 1, a headband 20 is represented with three electrodes mounted in the band. The inside of the band 21 includes a portion 23 which includes a network of hooks which secure into a network of fibers (not illustrated) on the outside 22 of the headband. Material known as VELCRO may be used to secure the headband but in its preferred form, the band element is composed of a material having some thickness with pliable and resilient characteristics so that the network of hooks 23 may be secured into the surface of the material upon over lap and slight pressure.

FIG. 3 shows, in sectional view the electrode and connecting circuitry along line A—A of FIG. 1. The circuitry element 25 includes one part 32 of a two part snap on fastener, the other part 30 of the fastener comprises the back plate or back disc of the electrode element. The open face flange or ring 50 is easily seen in FIG. 2 along with the teeth or prongs 51. Four such prongs 51, 51a 51b and 51c are illustrated in FIG. 2 although fewer or more prongs may be used, if desired.

The bottom disc or plate 30 is illustrated with four receiving slots 57, 57a, 57b and 57c, each slot for receiving one of the prongs on the perphery of the open face flange or ring 50. FIG. 3 illustrates the prongs (51 and 51a) extending through the conductive fabric 52 and the headband 20 from the inner surface 21 to the outer surface 22, passing through the slots 57 and bent or peened over so as to secure the open face flange 50 to the plate 30. Prior to peening the prongs, the open face flange 50 and the plate 30 are pressed together squeezing the captive material of the headband 20 between them. The inside surface of the plate 30 forces the captive material of the headband toward the opening 55 in the open face flange and because of the resiliency of the material, the material pushes out of the face opening 55 and forms a bubble or balloon which extend above the rim section of the ring or flange 50. Since the conductive fabric 52 is between the flange 50 and the headband 20 the conductive material covers the surface of the balloon formed by the headband material. The surface of the balloon is the conductive fabric and thus the conductive balloon is formed.

Preferably, the open face flange 50 and the prongs 51, a, b, and c and plate 30 are made of good conductor material. This may be metal or conductive plastic, for example. The conductive fabric 52 and the flange 50 and prongs 51 are all in good electric and physical contact with each other. The prongs 51 connected to the back plate 30 provide good electric contact between these elements. Thus, good electric contact is achieved between the electrode elements, i.e., the conductive fabric and the back plate, the flange or ring and the connectors.

Preferably, the plate 30 includes a stud of male section 31 of a two-part snap fastener 30/32. The member 32 includes a socket 33 adapted to receive and grip the stud 31. This accords good physical contact and good electrical contact between these elements. The part 32 may be mounted in a circuit retaining member 25. The circuit 26 may be a printed circuit, or large scale integration (LSI) chip which is connected via lead 27 to the socket or grip plate 32. The lead 40 may include one of more electric leads which are coupled to the LSI chip. The LSI chip 26 may be an amplifier circuit for amplifying the electric pulses picked up by the electrode.

FIG. 3a illustrates an alternate arrangement of the electrode where in the headband 20, with surfaces 21 and 22 and the conductive fabric 52, the open face flange 50 and prongs 51 are identical to the preferred structure. However, the members of the two-part fastener 30' and 32' are reversed in position, the socket plate 33' being located on the headband and connected to the open face flange 50 via the prong 51. In the alternate structure shown in FIG. 3a, the stud plate 30' of the two piece fastener is secured to the printed circuit retaining member 25 with the lead 27 extending from the terminal on the printed circuit to the stud plate 30' of the fastener.

When the headband 20 is secured snugly around the head of the patient, the conductive balloon electrode comes in to intimate contact with the surface of the skin and, according to how tight the band is, secured about the body part, tends to mushroom on the skin achieving good and broad surface electric contact with the skin, without discomfort.

Although the embodiments of the invention in FIGS. 3 and 3a illustrate prongs extending from the inner edge of the ring of the open face flange, it will be apparent that the prongs maybe extended from the outer edge of the ring. In addition, it is anticipated that screws could be substituted for prongs and serve the same purpose when the screws are threaded into receiving holes in the back disc or plate.

It will be appreciated that the flange or ring member may be in some other shape such as oval, octagonal or other geometric shape. The open face or area of the ring or flange although preferrably round may be oval or in some other shape, as desired. The under part of the ring or flange member, the part that makes physical contact with the conductive material is preferrably flat or slightly concave. This surface may be roughened if desired for making better physical and electric contact. The upper surface of the flange member may be any geometric shape but is illustrated curved, for convenience of illustration.

The use of a stretchable, conductive material is also anticipated. The height and/or size of the conductive balloon may depend on several factors, such as the thickness and resiliency of the material of the headband and how much pressure is exerted on the headband material when the open face flange and the bottom plate are secured and drawn together. The size of the opening in the flange is another factor.

Referring now to FIG. 3b the principles of the present invention are shown in a alternate embodiment of an electrode, illustrated in sectional view. FIG. 3b illustrates a ring or shoulder 62 covering part of the opening of a cylinder or skirt 60. The back plate is seen as a bottom element 61 which is drawn up the inside of the cylinder or skirt by turning the screws 63, the bottom plate or element 61 including tapped holes (not shown) to receive the screws. A mass or material 64 which has deformable, resilient characteristics is located within the cylinder or skirt 60, above the bottom element but generally held by the shoulder or ring 62. The mass or material 64 may be conductive material or conductive material, such as conductive fabric may be used to cover the deformable, resilient material 64 and thus cover the opening formed by the shoulder or ring 62, on the cylinder or skirt 60.

As the bottom element 61 is drawn toward the shoulder or ring 62, through the cylinder or skirt 60, the deformable, resilient material, which may be a conductive rubber for example, is pressed or squeezed between the bottom plate and the shoulder and part of the material is pressed out of the opening formed by the shoulder or ring 62, forming a balloon 65 extending above the surface of the shoulder or ring. If the material 64 is conductive, or if the material 64 is covered by a conductive material at the opening where the material 64 balloons through the opening formed by the ring 62, a conductive balloon 65 is formed.

As will be apparent, the shoulder or ring may be of conductive material, such as conductive metal or conductive plastic, for example. The cylinder or skirt, screws and bottom member may also be a conductive material. Thus, an unitary electrode element, employing the principles of the invention has been described. The structure of FIG. 3b may be fitted with an outer flange, such as 66, shown in broken line form. The electrode may be mounted in a band or strap which may hold the conductive balloon face of the electrode against the skin of a patient.

It is anticipated that the bottom member 61 may be in the form of a stud or a socket which maybe one part of a two-piece snap fastener.

The preferred embodiment of the invention has been shown and described along with alternate structures of the electrode. Several conductive materials have been mentioned and the preferred type of conductive fabric has been disclosed, without intending to limit the use of other possible materials. Other changes and modification of the invention may be made, as will be apparent to those skilled in the art, without departing from the spirit and scope of the invention as defined in the claims.

What is claimed is:

1. An electrode for making electrical contact with the skin of an individual, said electrode comprising:
   (a) a flange member having an open center area;
   (b) a plate member having spaced openings for receiving a connector means for securing said plate member to said flange member;
   (c) a connector means coupled to said flange member and spaced about said flange member for engaging said plate member through said spaced openings for connecting said flange member to said plate member;
   (d) an electrically conductive resilient material means positioned between said flange member and said plate member for covering said open center area; and,
   (e) a mass means positioned between said electrically conductive resilient material means and said plate member and held captive by said connector means and said plate member and said electrically conductive resilient material means, and said mass means forceably directed toward said open center area and out of said open center area by said plate member for forcing said electrically conductive resilient material means out of said open center area for forming an electrically conductive balloon above said open center area.

2. An electrode as in claim 1 and in which said flange member and said plate member and said connector means are each of electric conductor material.

3. An electrode as in claim 1 and in which said mass means has resilient characteristics.

4. An electrode as in claim 3 and in which said mass means is conductive.

5. An electrode as in claim 1 and in which said flange member and said plate member and said connector means and said mass means are each conductive.

6. An electrode as in claim 1 and in which said connector means are prongs and said spaced openings are slots.

7. An electrode as in claim 1 and in which said connector means are threaded screws and said spaced openings are tapped holes receiving said threaded screws.

8. An electrode as in claim 1 and in which said plate member further includes stud means extending from said plate member adapted to be inserted in a socket of a two piece stud/socket snap connector.

9. An electrode as in claim 1 and in which said conductive material is a metal conductor impregnated fabric.

10. An electrode as in claim 9 and in which said metal conductor impregnated fabric is silver impregnated cloth.

11. An electrode as in claim 1 and said electrode further includes a band means having length, width and thickness and said band means includes securing means at opposite ends of said length for securing said band means to a body part of an individual and said flange member is located on one side of said band means and said plate member is located on the other side of said band means and said connector means passes through said thickness of said band means securing a part of said thickness between said flange member and said plate member.

12. An electrode as in claim 11 and in which said mass means is a part of said band means.

13. An electrode as in claim 1 and in which at least said flange member is made of conductive plastic.

14. An electrode for making electrical contact with the skin of an individual, said electrode comprising:
   (a) a band means having length, width and thickness and at least a portion of said band means having resilience, and said band means having at least two matable parts for securing said band means around a body part for holding said electrode in contact with said skin;
   (b) a flange means mounted on a first side of said band means and having an open center area for permitting a part of said band means having resilience, to be forceably bulged out of said open center area;
   (c) a plate means mounted on a second side of said band means across from said flange means and essentially in alignment with said flange means, for exerting a force on said band means, across said thickness, for foreceably bulging part of said band means having resilience out of said open center area and, said plate means including spaced opening therein;
   (d) a connector means connected to said flange means and adapted to pass through said thickness of said band means, said connector means extending from said flange means to said plate means and into said spaced openings for connecting said plate means to said flange means and for securing a portion of said band means having resilience, between said flange means and said plate means; and,
   (e) a conductive means, in electrical contact with said flange means, positioned between said flange means and said first side of said band means and covering that part of said band means having resilience and forceably bulged out of said open center area of said flange means for forming a conductive balloon of said conductive means.

15. An electrode as in claim 13 and in which said connector means are prongs connected to and extending from said flange means.

16. An electrode as in claim 15 and in which said spaced openings in said plate means are slotted openings receiving said prongs.

17. An electrode as in claim 13 and in which said conductive means is a conductor impregnated fabric.

18. An electrode as in claim 17 and in which said conductor impregnated fabric is silver impregnated fabric.

19. An electrode as in claim 13 and in which said plate means includes stud means extending there from adapted to be inserted into the socket of a snap fastener.

20. An electrode as in claim 13 and in which said plate means includes socket means adapted to receive a stud means of a snap fastener.

21. An electrode as in claim 13 and in which said band means is a headband adapted to be secured around the head and hold said conductive balloon in electrical contact with the skin on the head.

22. An electrode as in claim 13 and in which said band means is a wrist band adapted to be secured around the wrist and hold said conductive balloon in electrical contact with the skin on said wrist.

23. An electrode as in claim 13 and in which said band means is a chest band adapted to be secured around the chest and hold said conductive balloon in electrical contact with the skin on said chest.

24. An electrode as in claim 13 and in which said band means is an arm band adapted to be secured around the arm and hold said conductive balloon in electrical contact with the skin on said arm.

25. A band mounted electrode for making contact with the skin of an individual, said band mounted electrode comprising:
   (a) band means having length and width, a first side and a second side and thickness there between and including coupling means on opposite ends of said length for securing said band means around a body part of said individual;
   (b) flange means having an open center area and positioned on said first side of said band means;
   (c) plate means having spaced openings therein and positioned on said second side of said band means;
   (d) connector means secured to said flange means and extending there from through said thickness of said band means toward said plate means and adapted to enter said spaced openings of said plate means for securing said flange means to said plate means and for securing part of said thickness of said band means between said flange means and said plate means; and
   (e) conductive means positioned between said flange means and said first side of said band means for covering said open center area, said conductive means being resilient and adapted for ballooning out of said open center area forceably by said thickness of said band means when said flange means and said plate means are secured together by said connector means.

26. A band mounted electrode as in claim 25 and in which said conductive means is a conductor impregnated fabric.

27. A band mounted electrode as in claim 26 and in which said conductor impregnated fabric is silver impregnated fabric.

28. A band mounted electrode as in claim 25 and in which said plate means further includes stud means extending from said plate means away from said band means and adapted to be inserted into the socket of a snap fastener.

29. A band mounted electrode as in claim 25 and in which said plate means further includes socket means adapted to receive a stud means of a snap fastener.

* * * * *